United States Patent
Abrams et al.

(10) Patent No.: US 11,529,615 B2
(45) Date of Patent: Dec. 20, 2022

(54) PROCESS FOR MAKING MODIFIED SMALL-CRYSTAL MORDENITE, TRANSALKYLATION PROCESS USING SAME, AND MODIFIED SMALL-CRYSTAL MORDENITE

(71) Applicant: UOP LLC, Des Plaines, IL (US)

(72) Inventors: Martha Leigh Abrams, Chicago, IL (US); Eseoghene Jeroro, Chicago, IL (US); Jaime G. Moscoso, Mount Prospect, IL (US); Deng-Yang Jan, Elk Grove Village, IL (US); Pelin Cox, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 95 days.

(21) Appl. No.: 17/196,369

(22) Filed: Mar. 9, 2021

(65) Prior Publication Data

US 2021/0187486 A1 Jun. 24, 2021

Related U.S. Application Data

(62) Division of application No. 16/419,271, filed on May 22, 2019, now Pat. No. 10,994,266.

(51) Int. Cl.
| | |
|---|---|
| *B01J 29/18* | (2006.01) |
| *B01J 29/80* | (2006.01) |
| *B01J 35/10* | (2006.01) |
| *C07C 6/12* | (2006.01) |
| *C07C 15/08* | (2006.01) |

(52) U.S. Cl.
CPC ............... *B01J 29/18* (2013.01); *B01J 29/80* (2013.01); *B01J 35/1042* (2013.01); *B01J 35/1057* (2013.01); *B01J 35/1061* (2013.01); *C07C 6/126* (2013.01); *C07C 15/08* (2013.01); *B01J 2229/16* (2013.01); *B01J 2229/24* (2013.01)

(58) Field of Classification Search
CPC ........ B01J 29/18; B01J 29/80; B01J 35/1042; B01J 35/1057; B01J 35/1061; B01J 2229/16; B01J 2229/24; B01J 35/1023; B01J 35/108; C07C 6/126; C07C 15/08; C07C 2529/70; Y02P 20/52
See application file for complete search history.

(56) References Cited

U.S. PATENT DOCUMENTS

| | | |
|---|---|---|
| 7,626,064 B1 | 12/2009 | Boldingh et al. |
| 7,687,423 B2 | 3/2010 | Moscoso et al. |
| 8,242,321 B2 | 8/2012 | Boldingh |
| 9,024,102 B2 | 5/2015 | Boldingh |
| 9,376,324 B2 | 6/2016 | Senderov et al. |

FOREIGN PATENT DOCUMENTS

| | | |
|---|---|---|
| EP | 2288673 A2 | 3/2011 |
| RU | 2288034 C1 | 11/2006 |
| WO | 2016094816 A1 | 6/2016 |

OTHER PUBLICATIONS

Tsai, et al., Base treated H-mordenite as stable catalyst in alkylbenezene transalkylation, The Royal Society of Chemistry, Green Chem., 2009, 11, 1349-1356.
Tsai, et al., Study on optimum base-treatment of mordenite for catalytic alkylbenzene transalkylation, Catalysis Today, 259, 2016, 423-429.
Groen, Johan C., et al., Alkaline-mediated mesoporous mordenite zeolites for acid-catalyzed conversions, Journal of Catalysis 251, 2007, 21-27.
Ivanova I.I. et al., Design of micro/mesoporous zeolite-based catalysts for petrochemical and organic synthesis, Kinetics and Catalysis, 56, 549-561 (2015).
International Search Report for PCT application No. PCT/US2020/032586, dated Aug. 27, 2020.
Written Opinion for PCT application No. PCT/US2020/032586, dated Aug. 27, 2020.

*Primary Examiner* — Thuan D Dang

(57) ABSTRACT

A modified UZM-14 zeolite is described. The modified UZM-14 zeolite has a Modification Factor of 6 or more. The modified UZM-14 zeolite may have one or more of: a $Si/Al_2$ ratio of 14 to 30; a total pore volume in a range of 0.5 to 1.0 cc/g; at least 5% of a total pore volume being mesopores having a diameter of 10 nm of less; a cumulative pore volume of micropores and mesopores having a diameter of 100 Å or less of 0.25 cc/g or more; or a Collidine IR Bronsted acid site distribution greater than or equal to an area of 3/mg for a peak in a range of 1575 to 1700 $cm^{-1}$ after desorption at 150° C. Processes of making the modified UZM-14 zeolite and transalkylation processes using the modified UZM-14 zeolite are also described.

13 Claims, 5 Drawing Sheets

PROCESS FOR MAKING MODIFIED SMALL-CRYSTAL MORDENITE, TRANSALKYLATION PROCESS USING SAME, AND MODIFIED SMALL-CRYSTAL MORDENITE

CROSS-REFERENCE TO RELATED APPLICATIONS

This application is a Divisional of U.S. patent Ser. No. 16/419,271 filed on May 22, 2019, the contents of which cited application is hereby incorporated by reference in its entirety.

BACKGROUND

Xylene isomers are produced in large volumes from petroleum as feedstocks for a variety of important industrial chemicals. The most important of the xylene isomers is para-xylene, the principal feedstock for polyester which continues to enjoy a high growth rate from a large base demand. Ortho-xylene is used to produce phthalic anhydride, which has high-volume but mature markets. Meta-xylene is used in lesser but growing volumes for such products as plasticizers, azo dyes, and wood preservers. Ethylbenzene is typically present in xylene mixtures and is occasionally recovered for styrene production, but is usually considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand. Consequently, conversion of other hydrocarbons is necessary to increase the yield of xylenes and benzene. Toluene is commonly dealkylated to produce benzene or disproportionated to yield benzene and $C_8$ aromatics from which the individual xylene isomers are recovered. More recently, processes have been commercialized to transalkylate heavier aromatics along with toluene selectively to increase the yield of xylenes from aromatics complexes.

The art teaches a variety of catalysts for the transalkylation of aromatic hydrocarbons. A wide range of zeolites, including mordenite, have been disclosed as effective transalkylation catalysts. Shaped catalysts, multiple zeolites, metal modifiers, and treatments such as steam calcination have been described as pathways for increasing the effectiveness of the catalysts. There is a need to improve catalyst stability and the conversion of heavy material.

DESCRIPTION OF THE INVENTION

Figure 1:
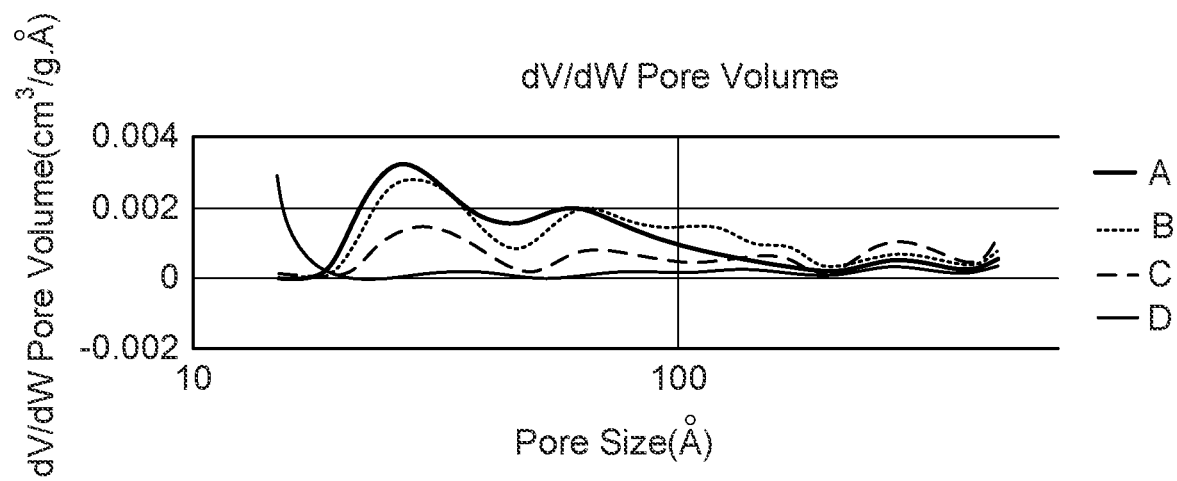
FIG. 1 is graph comparing the pore size distribution (dV/dW Pore Volume) of several modified UZM-14 zeolites with the UZM-14 zeolite.

This invention involves the development of a unique modified UZM-14 material (designated UZM-14M). UZM-14M has a $Si/Al_2$ ratio of at least 15 to about 30, and a total pore volume between 0.5 and 1.0 cc/g where at least 5% of the total pore volume is in mesopores with diameters less than 10 nm as derived from $N_2$ adsorption measurement using DFT isotherm modeling. It also exhibits a high mesoporosity with high retention of micropores, as defined by a "Modification Factor" greater than 6. The Modification Factor (MF) is equal to (Volume of mesopores of 20-100 Å in modified material/Volume of mesopores of 20-100 Å in unmodified parent material)×(Volume of micropores in modified material/Volume of micropores in unmodified parent material)).

Additionally, the Bronsted acidity of the UZM-14M zeolite measured by Collidine IR analysis is increased compared to that of the parent material due to the increased accessibility to acid sites in the zeolite. UZM-14M differs from unmodified UZM-14 because the additional internal mesopores in the UZM-14M zeolite enhances the performance of a catalyst incorporating this zeolite in the transalkylation process, particularly when the transalkylation process involves heavy feedstocks. The UZM-14M zeolite provides improved performance in transalkylation, for example, an increase in the xylene selectivity of 0.5-2.0% compared to UZM-14 and an increase in phenyl retention of 0.2 mol % as measured by a standard pilot plant test described in U.S. Pat. No. 7,626,064 using a feed of 50 wt % toluene/50 wt % A9+ aromatics.

The properties of the UZM-14M zeolite are listed below. The total pore volume is at least 0.5 cc/g. The cumulative pore volume of micropores and mesopores less than 100 Å is at least 0.25 cc/g. The ratio of $Si/Al_2$ is in the range of 14 to 30, or 16 to 30, or 18 to 30, or 20 to 30, or 22 to 30, or 23 to 30, or 23 to 29. The distribution of Bronsted acid sites measured by Collidine IR analysis is greater than or equal to an area of 3/mg for the peak at 1635 $cm^{-1}$ (between 1575 to 1700 $cm^{-1}$) after desorption at 150° C.

One aspect of the invention is a process for making a modified UZM-14 zeolite. In one embodiment, the process comprises: contacting a calcined UZM-14 zeolite with one or more of: nitric acid, or oxalic acid to form an acid washed UZM-14 zeolite; contacting the acid washed UZM-14 with one or more of: a sodium hydroxide solution, or a sodium bicarbonate solution to form a caustic washed UZM-14 zeolite; and ion exchanging the caustic washed zeolite to form the modified UZM-14 zeolite.

In some embodiments, the calcined UZM zeolite is formed by calcining a UZM-14 material to remove an organic template.

In some embodiments, the modified UZM-14 has a Modification Factor of 6 or more.

In some embodiments, the modified UZM-14 has a $Si/Al_2$ ratio of 14 to 30.

In some embodiments, the modified UZM-14 has a total pore volume in a range of 0.5 to 1.0 cc/g.

In some embodiments, the modified UZM-14 has at least 5% of a total pore volume being mesopores having a diameter of 10 nm of less.

In some embodiments, the modified UZM-14 has a cumulative pore volume of micropores and mesopores having a diameter of 100 Å or less of 0.25 cc/g or more.

In some embodiments, the modified UZM-14 has a Collidine IR Bronsted acid site distribution greater than or equal to an area of 3/mg for a peak in a range of 1575 to 1700 cm$^{-1}$ after desorption at 150° C.

Another aspect of the invention is a process for transalkylation. In one embodiment, the process involves contacting a feedstream comprising one or more of $C_7$, $C_9$, $C_{10}$ and $C_{11+}$ aromatics at transalkylation conditions with a catalyst to obtain a product stream having an increased concentration of $C_8$ aromatics relative to that of the feedstream, the catalyst comprising: (a) a modified UZM-14 zeolite having a Modification Factor of 6 or more; (b) a binder selected from one or more of alumina, silica and silica-alumina; and, (c) a metal component comprising one or more elements selected from groups VIB(6), VIIB(7), VIII(8-10) and IVA(14) of the Periodic Table.

In some embodiments, the modified UZM-14 zeolite has one or more of: a $Si/Al_2$ ratio of 14 to 30; a total pore volume in a range of 0.5 to 1.0 cc/g; at least 5% of a total pore volume are mesopores having a diameter of 10 nm of less; a cumulative pore volume of micropores and mesopores having a diameter of 100 Å or less of 0.25 cc/g or more; or a Collidine IR Bronsted acid site distribution greater than or equal to an area of 3/mg for a peak in a range of 1575 to 1700 cm$^{-1}$ after desorption at 150° C.

In some embodiments, the feedstream further comprises benzene.

In some embodiments, the feedstream further comprises $C_8$ aromatics.

In some embodiments, the feedstream further comprises aromatic compounds having from 2 to 4 rings.

In some embodiments, the feedstream further comprises a bottoms stream from the fractionation of $C_8$ aromatics from the transalkylation product stream.

In some embodiments, the transalkylation conditions comprise one or more of: a temperature from about 200° C. to about 540° C., a pressure from about 100 kPa to about 6 MPa absolute, or a space velocity from about 0.1 to about 20 hr$^{-1}$.

Another aspect of the invention is a catalyst suitable for the conversion of aromatic hydrocarbons. In one embodiment, the catalyst comprises: a modified UZM-14 zeolite having a Modification Factor of 6 or more.

In some embodiments, the modified UZM-14 zeolite has one or more of: a $Si/Al_2$ ratio of 14 to 30; a total pore volume in a range of 0.5 to 1 cc/g; at least 5% of a total pore volume being mesopores having a diameter of 10 nm of less; a cumulative pore volume of micropores and mesopores having a diameter of 100 Å or less of 0.25 cc/g or more; or a Collidine IR Bronsted acid site distribution of greater than or equal to an area of 3/mg for a peak in a range of 1575 to 1700 cm$^{-1}$ after desorption at 150° C.

In some embodiments, the catalyst further comprises: (a) a binder selected from one or more of alumina, silica and silica-alumina; and, (b) a metal component comprising one or more elements selected from groups VIB(6), VIIB(7), VIII(8-10) and IVA(14) of the Periodic Table.

The process of preparing the modified UZM-14 small-crystal mordenite involves several steps. UZM-14 can be prepared according to the process described in U.S. Pat. Nos. 7,626,064 and 7,687,423, for example, which are incorporated herein by reference in its entirety.

The as-synthesized UZM-14 material is calcined. Suitable calcination conditions include a temperature in the range of 400 to 750° C. or 425 to 550° C. for 0.5 to 10 hours or 2 to 8 hours. Complete calcination can be determined using CHN analysis to ensure all of the C and N have been removed. The calcined UZM-14 has an $Si/Al_2$ ratio of about 18.

The calcined UZM-14 zeolite is contacted with nitric acid or oxalic acid to form an acid washed UZM-14 zeolite. The calcined UZM-14 zeolite can be contacted at a temperature of 45 to 75° C. for 2 to 6 hours. The acid wash increases the $Si/Al_2$ ratio to the 30 to 45 range. The acid wash determines the extent of the caustic modification.

The acid washed UZM-14 is contacted with a sodium hydroxide solution or sodium bicarbonate solution to form a caustic washed UZM-14 zeolite. The acid-washed UZM-14 zeolite can be contacted from room temperature to 65° C. for 2 to 6 hours. The caustic wash reduces the $Si/Al_2$ ratio and introduces the desired mesoporosity.

The caustic washed zeolite is ion exchanged to form the modified UZM-14M zeolite. The caustic washed zeolite is contacted with an ammonium salt, including but not limited to, ammonium nitrate, ammonium chloride, ammonium sulfate, and the like at a temperature of 70 to 80° C. for 2 to 6 hours. The ion exchanged UZM-14 retains most of the microporous volume, and has increased total pore volume due to the increased mesoporosity.

After the ion exchange, UZM-14M can be used in a catalyst preparation. It can be combined with one of more of other zeolites, binders, and metals as described below.

The catalyst of the invention comprises a refractory inorganic-oxide binder and a metal component. The catalyst also preferably has been subjected to a pre-sulfiding step to incorporate from about 0.05 to about 3 wt.-% sulfur on an elemental basis.

The inorganic-oxide binder component of the invention comprises such materials as alumina, silica, zirconia, titania, thoria, boria, magnesia, chromia, stannic oxide, and the like as well as combinations and composites thereof, for example alumina-silica, alumina-zirconia, alumina-titania, aluminum phosphate, and the like. The binder preferably is selected from one or more of alumina, silica and silica-alumina. Alumina is an especially preferred refractory inorganic oxide for use herein, particularly with respect to the manufacture of a catalytic composite for use in the transalkylation of alkylaromatic hydrocarbons. The alumina may be any of the various hydrous aluminum oxides or alumina gels such as alpha-alumina monohydrate of the boehmite structure, alpha-alumina trihydrate of the gibbsite structure, beta-alumina trihydrate of the bayerite structure, and the like, the first mentioned alpha-alumina monohydrate being preferred. An alternative preferred binder is aluminum phosphate as described in U.S. Pat. No. 4,629,717 which is incorporated herein by reference.

The binder and zeolite may be combined in any conventional or otherwise convenient manner to form spheres, pills, pellets, granules, extrudates, or other suitable particle shape. For example, finely divided zeolite and metal salt particles can be dispersed in an alumina sol, and the mixture in turn dispersed as droplets in a hot oil bath whereby gelation occurs with the formation of spheroidal gel particles. The method is described in greater detail in U.S. Pat. No. 2,620,314. A preferred method comprises comingling a finely divided form of the selected zeolite, refractory inorganic oxide and a metal salt with a binder and/or lubricant and compressing the mixture into pills or pellets of uniform size and shape. Alternatively, and still more preferably, the zeolite, refractory inorganic oxide and metal salt are combined and admixed with a peptizing agent in a mix-muller, a dilute nitric acid being one example of the suitable peptizing agent. The resulting dough can be pressured through a die or orifice of predetermined size to form extrudate particles which can be dried and calcined and utilized as such. A multitude of different extrudate shapes are possible, including, but not limited to, cylinders, cloverleaf, dumbbell and symmetrical and asymmetrical polylobates, with a trilobe form being favored. The extrudates also may be formed into spheres by means of a spinning disc or drum and then dried and calcined.

The catalyst of the invention optionally may comprise an additional zeolitic component. The additional zeolite component preferably is selected from one or more of MFI, MEL, EUO, FER, MFS, MOR, MTT, MTW, MWW, MAZ, TON and FAU (IUPAC Commission on Zeolite Nomenclature). More preferably, particularly when the catalyst is used in a transalkylation process, the additional zeolitic component consists essentially of MFI. Suitable total zeolite amounts in the catalyst range from about 1 to about 100 wt-%, preferably from about 10 to about 95 wt-%, and more preferably between about 60 and about 90 wt-%.

The catalyst preferably comprises a metal component comprising one or more elements selected from groups VIB(6), VIIB(7), VIII(8-10), and IVA(14) of the Periodic Table. Preferably the metal component is selected from one or more of nickel, cobalt, rhenium, molybdenum and tungsten when the catalyst is used in a transalkylation process. The catalyst also may contain phosphorus. Suitable metal amounts in the transalkylation catalyst range from about 0.01 to about 15 wt-% on an elemental basis, with the range from about 0.1 to about 12 wt-% being preferred, and the range from about 0.1 to about 10 wt-% being highly preferred. The catalyst also preferably has been subjected to a presulfiding step to incorporate from about 0.05 to about 2 wt.-% sulfur on an elemental basis. This presulfiding step may take place either during the manufacture of the catalyst or after the catalyst has been loaded into a process unit.

The finished composite is preferably calcined in an air atmosphere at a temperature of from about 425° C. to about 750° C., preferably at a temperature of from about 475° C. to about 550° C., over a period of from about 0.5 to about 10 hours.

The feedstream to the present process comprises alkylaromatic hydrocarbons of the general formula $C_6H_{(6-n)}R_n$, where n is an integer from 0 to 5 and R is $CH_3$, $C_2H_5$, $C_3H_7$, or $C_4H_9$, in any combination. Suitable alkylaromatic hydrocarbons include, for example but without so limiting the invention, benzene, toluene, ortho-xylene, meta-xylene, para-xylene, ethylbenzene, ethyltoluenes, propylbenzenes, tetramethylbenzenes, ethyl-dimethylbenzenes, diethylbenzenes, methylpropylbenzenes, ethylpropylbenzenes, triethylbenzenes, diisopropylbenzenes, and mixtures thereof.

The aromatics-rich feed stream to a transalkylation or disproportionation process may be derived from a variety of sources, including without limitation catalytic reforming, pyrolysis of naphtha, distillates or other hydrocarbons to yield light olefins and heavier aromatics-rich byproducts, and catalytic or thermal cracking of heavy oils to yield products in the gasoline range. Products from pyrolysis or other cracking operations generally will be hydrotreated according to processes well known in the industry before being charged to the complex in order to remove sulfur, nitrogen, olefins and other compounds which would affect product quality. Light cycle oil also may be beneficially hydrocracked to yield lighter components which can be reformed catalytically to yield the aromatics-rich feed stream. If the feed stream is catalytic reformate, the reformer preferably is operated at high severity for high aromatics yield with a low concentration of non-aromatics in the product. The reformate also advantageously is subjected to olefin saturation to remove potential product contaminants and materials that could polymerize to heavy non-convertibles in a transalkylation process. Such processing steps are described in U.S. Pat. No. 6,740,788 B1, incorporated herein by reference thereto.

The feed stream to a transalkylation or disproportionation process can be a substantially pure alkylaromatic hydrocarbon of from about 6 to about 15 carbon atoms, a mixture of such alkylaromatic hydrocarbons, or a hydrocarbon fraction rich in said alkylaromatics. The feed stream comprises alkylaromatic hydrocarbons of the general formula $C_6H_{(6-n)}R_n$, where n is an integer from 1 to 5 and R is one or more of $CH_3$, $C_2H_5$, $C_3H_7$, $C_4H_9$, or $C_5H_{11}$ in any combination. The feed stream also may comprise benzene and aromatics having from 2 to 4 rings. Suitable components of the feed stream thus generally include, for example but without so limiting the invention, benzene, toluene, ethylbenzene, meta-xylene, ortho-xylene, para-xylene, ethyl-toluenes, trimethylbenzenes, diethyl-benzenes, triethylbenzenes, propylbenzenes, butylbenzenes, methylpropylbenzenes, ethylpropylbenzenes, diisopropylbenzenes, butylbenzenes, indanes, naphthalenes, tetralins, decalins, biphenyls, diphenyls and fluorenes. The feed stream also may contain lesser concentrations of nonaromatics such as pentanes, hexanes, heptanes and heavier paraffins, along with methylcyclopentane, cyclohexane and heavier naphthenes; pentanes and lighter paraffins generally will have been removed before processing in the aromatics complex. The combined transalkylation feed preferably contains no more than about 10 wt-% nonaromatics; olefins preferably are restricted to a Bromine Index of no more than about 1500, and preferably no more than about 500.

A preferred component of the feedstock is a heavy-aromatics stream comprising $C_9$ aromatics, thereby effecting transalkylation of toluene and $C_9$ aromatics to yield additional xylenes. Benzene may also be transalkylated to yield additional toluene. Indane may be present in the heavy-aromatics stream, although it is not a desirable component to effect high yields of $C_8$ aromatics product. $C_{10+}$ aromatics also may be present, preferably in an amount of 30% or less of the feed. The heavy-aromatics stream preferably comprises at least about 90 mass-% aromatics, and may be derived from the same or different known refinery and petrochemical processes as the benzene and toluene feedstock and/or may be recycled from the separation of the product from transalkylation.

The feedstock is typically transalkylated in the vapor phase and in the presence of hydrogen. If transalkylated in the liquid phase, then the presence of hydrogen is optional. If present, free hydrogen is associated with the feedstock and recycled hydrocarbons in an amount of from about 0.1 moles per mole of alkylaromatics up to 10 moles per mole of alkylaromatics. This ratio of hydrogen to alkylaromatics is also referred to as hydrogen to hydrocarbon ratio. The transalkylation reaction preferably yields a product having an increased xylene content and also comprises benzene.

The feed to a transalkylation reaction zone usually first is heated by indirect heat exchange against the effluent of the reaction zone and then is heated to reaction temperature by exchange with a warmer stream, steam or a furnace. The feed then is passed through a reaction zone, which may comprise one or more individual reactors. Passage of the combined feed through the reaction zone effects the production of an effluent stream comprising unconverted feed and product hydrocarbons. This effluent is normally cooled by indirect heat exchange against the stream entering the reaction zone and then further cooled through the use of air or cooling water. The effluent may be passed into a stripping column in which substantially all $C_5$ and lighter hydrocarbons present in the effluent are concentrated into an overhead stream and removed from the process. An aromatics-rich stream is recovered as net stripper bottoms which is referred to herein as the transalkylation effluent.

The transalkylation or disproportionation reaction can be effected in contact with the catalytic composite of this invention in any conventional or otherwise convenient manner and may comprise a batch or continuous type of operation, with a continuous operation being preferred. The catalyst usefully is disposed as a fixed bed in a reaction zone of a vertical tubular reactor with the alkylaromatic feed stock charged through the bed in an upflow or downflow manner.

Conditions employed in the transalkylation zone normally include a temperature of from about 200° C. to about 540° C., preferably between about 200° C. to about 480° C. The transalkylation zone is operated at moderately elevated pressures broadly ranging from about 100 kPa to about 6 MPa absolute. The transalkylation reaction can be effected over a wide range of space velocities, i.e., weight of charge per weight of catalyst per hour, weight hourly space velocity generally is in the range of from about 0.1 to about 20 $hr^{-1}$.

The transalkylation effluent is separated into a light recycle stream, a mixed $C_8$ aromatics product and a heavy-aromatics stream. The mixed $C_8$ aromatics product can be sent for recovery of para-xylene and other valuable isomers. The light recycle stream may be diverted to other uses such as to benzene and toluene recovery, but alternatively is recycled partially to the transalkylation zone. The heavy recycle stream contains substantially all the $C_9$ and heavier aromatics and may be partially or totally recycled to the transalkylation reaction zone.

EXAMPLES

Example 1—Preparation of the UZM-14M Zeolite 230 g of as-synthesized UZM-14 material was placed into a ceramic dish. The material was heated in an oven at a rate of 2° C./min to a temperature of 580° C. with 300 SCFH of air. It was held at 580° C. for 6 hours with 300 SCFH of air. The calcined sample was tested using CHN analysis to ensure all the C and N had been removed.

2376.6 g of water and 456.9 g of 70% nitric acid were placed in a stainless-steel beaker and mixed at 150 RPM. 300 g of calcined UZM-14 were added to the beaker. The stir plate was heated to 75° C. and the slurry was held at 75° C. for 4 hours. The beaker was removed from the stir plate. The slurry was filtered over a Buchner funnel using filter paper type 52. Once the acid solution had been filtered through, the filtrate was rinsed with 2500 ml of water to remove any residual acid. The material was air dried. The solid samples were ground.

2600.2 g of water and 151.2 g of 50% NaOH were placed in a stainless-steel beaker and mixed at 150 RPM. Add 270 g of acid washed UZM-14 was added to the beaker. The slurry was held at room temperature for 3.5 hours. The beaker was removed from the stir plate, and the slurry was filtered over a Buchner funnel using filter paper type 52. Once the caustic solution had been filtered through, the filtrate was rinsed with 2500 ml of water to remove any residual base. The sample was air dried and ground.

2573.8 g of water and 217.2 g of ammonium nitrate powder were added to a stainless-steel beaker. 200 g of caustic washed UZM-14 was added to the beaker. The stir plate was heated to 75° C. and the slurry was held at 75° C. for 1 hour. The beaker was removed from the stir plate, and the slurry was filtered over a Buchner funnel using filter paper type 52. Once the nitrate solution was filtered through, the ion exchanged material was rinsed with 2500 ml of water to remove any excess nitrates. The ion exchange was repeated two more times. The sample was re-slurried for each ion exchange. After the water washing was complete, the sample was dried at 100° C. overnight. The solid sample was ground.

Example 2—Preparation of Catalyst Containing the UZM-14M Zeolite

A powder blend made up of UZM-14 or UZM-14M, any additional zeolites, and the binder was placed in a muller and dry mulled for about 15 minutes. A nitric acid solution of about 18-20 wt % was subsequently added to the powder blend and mulled for about 15 minutes. An ammonium heptamolybdate (AHM) solution was added and the mixture containing the powder blend, nitric acid solution, and AHM solution was mulled for about 15 minutes. An additional amount of water was added to the aforementioned mixture to obtain an LOI (Loss of Ignition) of between 35 to 50 wt % to attain an extrudable dough consistency.

The dough was extruded through a die plate containing die holes with a diameter in the range of ¹⁄₃₂ to ⅛ inches, and the green extrudate was collected and dried at 100° C. for 2 to 12 hours.

The dried extrudate base was sized to 10×12 mesh and then calcined at a temperature between 500 and 580° C. for 4 hours in a box oven.

Example 3—Properties of the UZM-14M Zeolites

Figure 2:
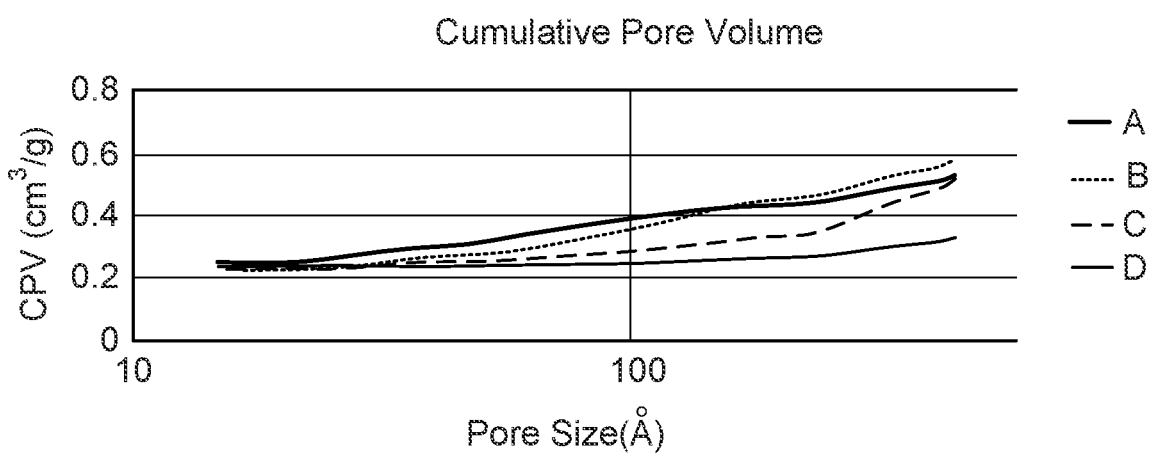
FIG. 2 is graph comparing the cumulative pore volume of several modified UZM-14 zeolites with the UZM-14 zeolite.

Properties of UZM-14M Samples A, B, and C made using the procedure described in Example 1 are summarized in Table 1. Properties of a reference unmodified UZM-14 Sample D are also included. The values in this table were calculated from the DFT dV/dW and Cumulative pore volume data shown in FIGS. 1 and 2. The UZM-14M samples have a higher total pore volume (in the range of 0.5-1.0 cc/g) range compared to the unmodified UZM-14 sample, and their Modification Factors are greater than 6. The increase in mesoporous and total pore volume reduces diffusional limitations within the zeolite structure, which increases xylene selectivity in the transalkylation reaction by making it easier for the feed molecules to access the active site. In some instances, additional pore volume generated in the 1-2 nm pore size range is incorporated into the micropore volume measurement, leading to a greater micropore volume than in the parent material.

TABLE 1

| Zeolite sample | A | B | C | D |
|---|---|---|---|---|
| Total pore volume (Vtot) | 0.671 | 0.737 | 0.840 | 0.405 |
| Cumulative Pore Volume <100 Å from DFT | 0.384 | 0.350 | 0.279 | 0.244 |
| Micropore volume from DFT (Vmicro) | 0.246 | 0.221 | 0.225 | 0.235 |
| BET Surface Area | 648 | 591 | 563 | 556 |
| Pore volume in 20-100 Å range from DFT (Vmeso) | 0.138 | 0.129 | 0.055 | 0.009 |

TABLE 1-continued

| Zeolite sample | A | B | C | D |
|---|---|---|---|---|
| Vmicro*Vmeso | 0.034 | 0.029 | 0.012 | 0.002 |
| Vmeso/Vtot | 0.206 | 0.176 | 0.065 | 0.021 |
| Vmicro/Vtot | 0.367 | 0.300 | 0.267 | 0.580 |
| Modification Factor (DFT) | 17.0 | 14.3 | 6.1 | 1.0 |
| UZM-14M Vmicro/UZM-14 Vmicro | 1.0 | 0.9 | 1.0 | 1.0 |
| UZM-14M Vmeso/UZM-14 Vmeso | 16.2 | 15.2 | 6.4 | 1.0 |

DFT pore volumes were calculated from the nitrogen adsorption isotherms using MicroActive software with the Tarazona method and a smoothing regularization of 0.316. BET surface areas were calculated using the Roquerol modification and points at P/Po of ~0.01-0.04, and t-plot using a thickness of 3.5-5.0 Å.

Example 4—Test Results of UZM-14M Catalysts with a Toluene and Heavy Aromatics Feed Three catalysts (A, B, C) were made using UZM-14M prepared according to the procedure described in Example 2. A reference catalyst (D) was made using unmodified UZM-14 following the same formulation and procedure. The catalyst composition was 49.05 wt % modified or unmodified UZM-14, 24.54 wt % MFI, 24.54 wt % alumina, and 1.84 wt % AHM. The catalysts were tested in a transalkylation reaction using a feed of 50 wt % toluene and 50 wt % A9+ aromatics. The transalkylation reaction conditions were a WHSV of 3.5 $hr^{-1}$, a molar ratio of hydrogen to feed of 3, a pressure of 2.8 MPa(g) (400 psig), and temperatures from 310° C. to 360° C. The results were compared at a target overall A7/A9/A10 conversion of 48 wt %.

Figure 3:
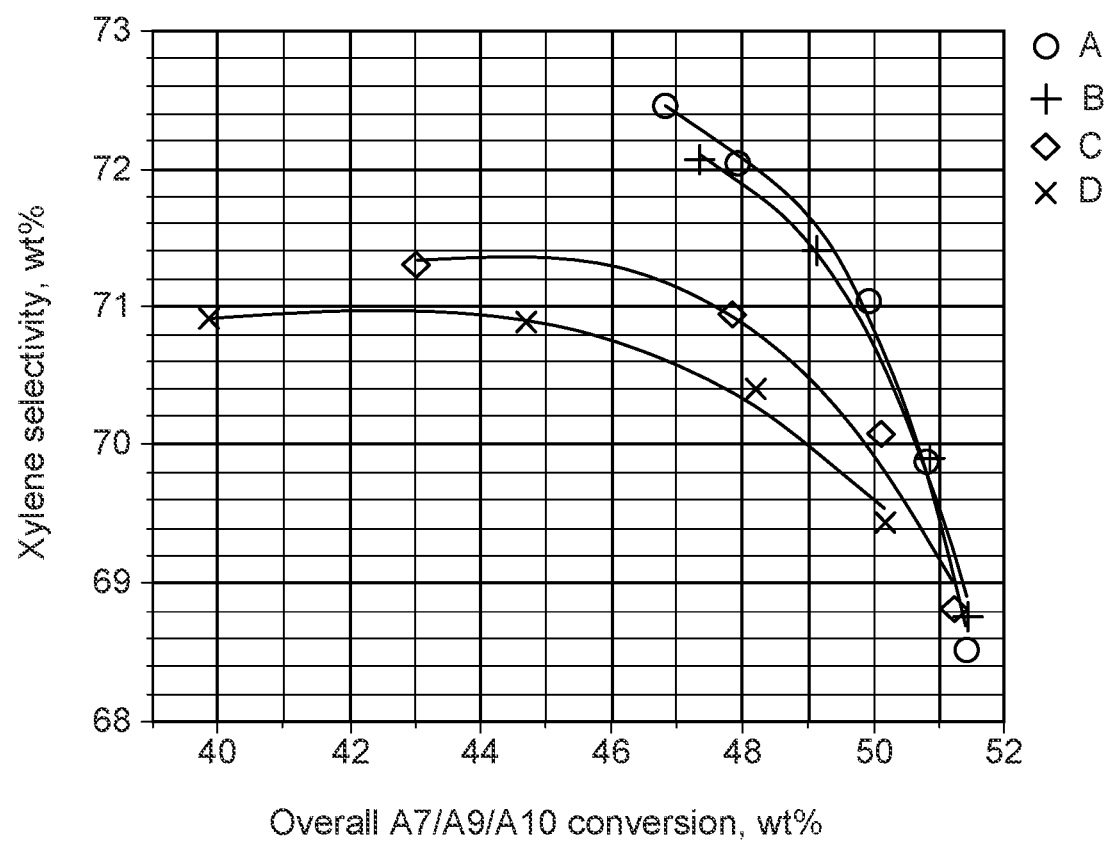
FIG. 3 is graph comparing the xylene selectivity of several modified UZM-14 catalysts with the UZM-14 catalyst.
Figure 4:
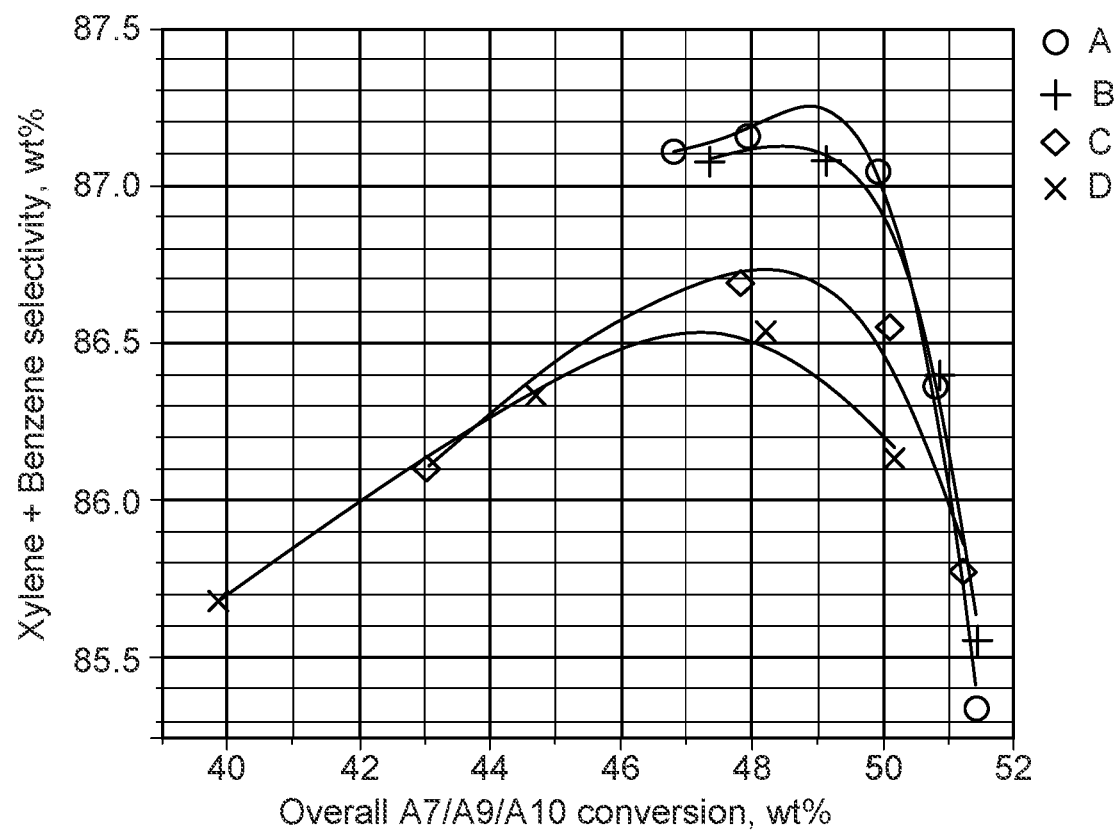
FIG. 4 is graph comparing the xylene+benzene selectivity of several modified UZM-14 catalysts with the UZM-14 catalyst.
Figure 5:
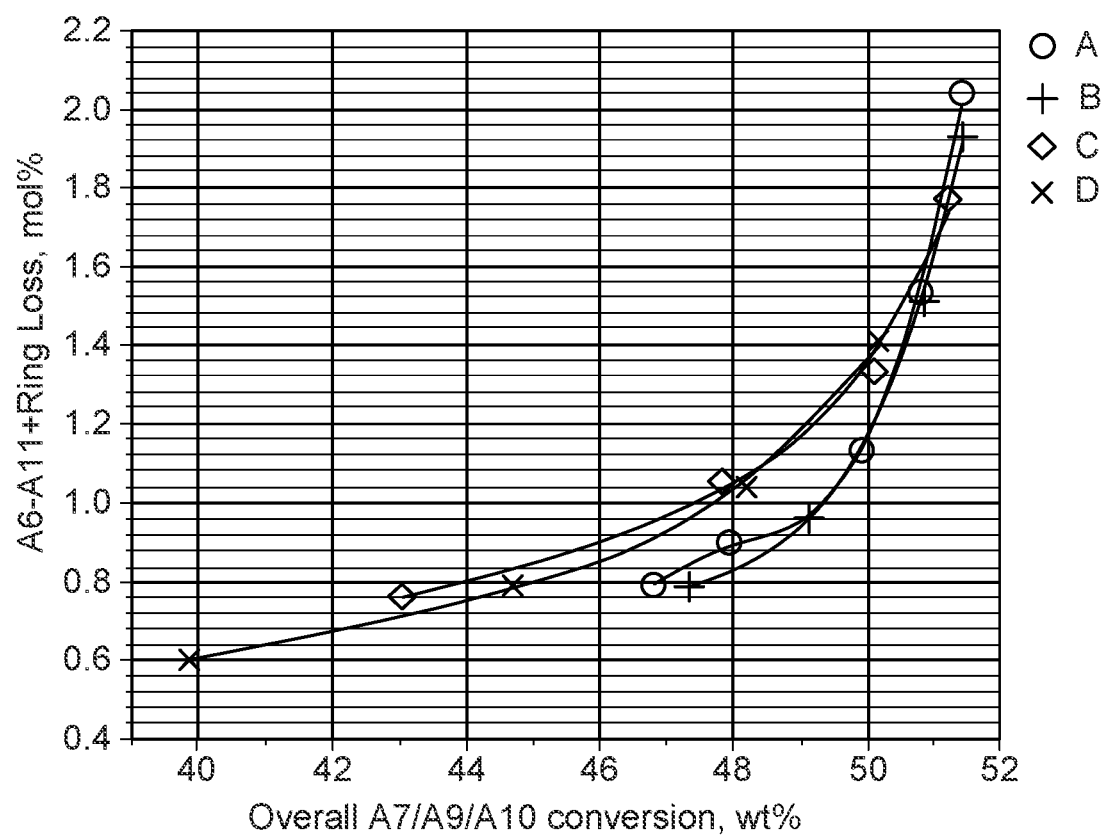
FIG. 5 is graph comparing the aromatic ring loss of several modified UZM-14 catalysts with the UZM-14 catalyst.

FIGS. 3-5 show the results of the transalkylation reactions. Compared with the catalyst containing UZM-14 (D), the catalysts made up of UZM-14M (A, B, C) showed increased xylene selectivity and increased xylene+benzene selectivity, as shown in FIGS. 3-4. Two UZM-14M catalysts (A, B) showed lower aromatic ring losses than the UZM-14 catalyst (D), and one (C) was comparable, as shown in FIG. 5. The higher mesoporous and total pore volume of the UZM-14M zeolites in Table 1 is responsible for the higher xylene selectivity, and a higher xylene and benzene selectivity in the transalkylation reaction. The UZM-14M zeolite can also decrease the $C_6$ to $C_{11}$+ aromatic ring loss (increase phenyl retention) in the transalkylation reaction compared to the catalyst made with unmodified UZM-14.

Figure 6:
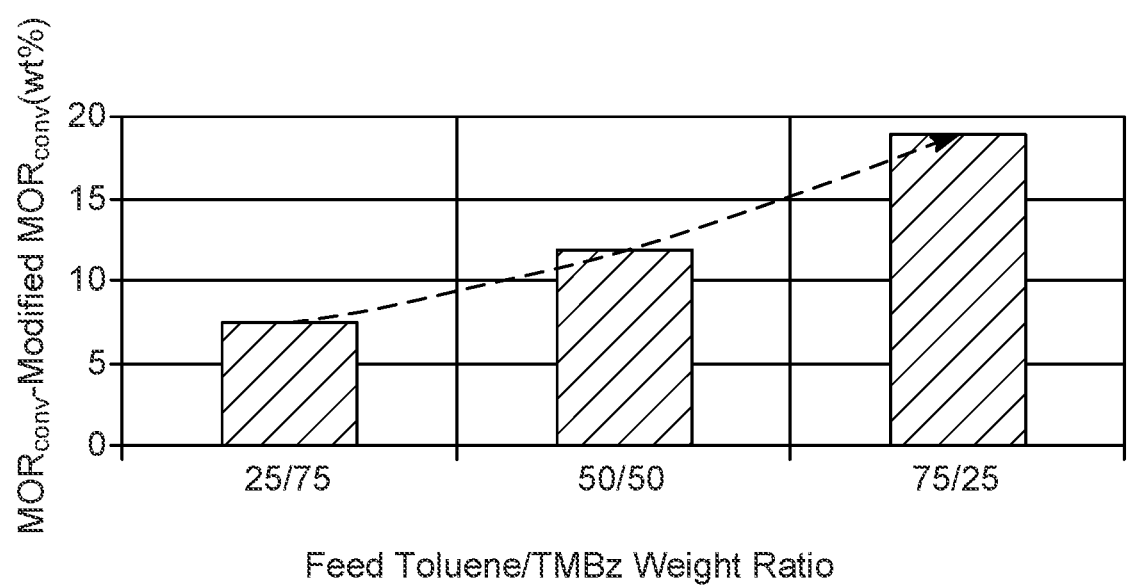
FIG. 6 is a graph showing the impact of feed composition on the conversion in the toluene and trimethylbenzene transalkylation reaction.

Example 5—Test Results of UZM-14M Catalysts with Toluene and Trimethylbenzene Feeds FIG. 6 shows the differences in overall A7+-A9 conversion observed in the transalkylation of trimethylbenzene (TMBz) with toluene for a catalyst made up of UZM-14M and alumina at a formulation of 70/30 on a weight basis relative to a catalyst made up of unmodified UZM-14 of the same formulation. Both catalysts were made following the process in Example 2. Test conditions are under liquid phase conditions: a WHSV of 2 $hr^{-1}$, a molar hydrogen to feed ratio of 0.15, a pressure of 3.4 MPa(g) (500 psig), and a temperature of 300° C. An increase in overall conversion was observed for the UZM-14M catalyst over a wide range of toluene/TMBz feed compositions. Furthermore, the magnitude of the improvement increases with increased contents of toluene in the feed blend. This shows that the benefits of the UZM-14M catalyst materialize over a wide range of feed compositions and are especially evident with a higher concentration of toluene compared to heavier (A9+) aromatics.

Specific Embodiments

While the following is described in conjunction with specific embodiments, it will be understood that this description is intended to illustrate and not limit the scope of the preceding description and the appended claims.

A first embodiment of the invention is a process for making a modified UZM-14 zeolite comprising contacting a calcined UZM-14 zeolite with one or more of nitric acid, or oxalic acid to form an acid washed UZM-14 zeolite; contacting the acid washed UZM-14 with one or more of a sodium hydroxide solution, or a sodium bicarbonate solution to form a caustic washed UZM-14 zeolite; and ion exchanging the caustic washed zeolite to form the modified UZM-14 zeolite. An embodiment of the invention is one, any or all of prior embodiments in this paragraph up through the first embodiment in this paragraph wherein the calcined UZM zeolite is formed by calcining a UZM-14 material to remove an organic template. An embodiment of the invention is one, any or all of prior embodiments in this paragraph up through the first embodiment in this paragraph wherein the modified UZM-14 has a Modification Factor of 6 or more. An embodiment of the invention is one, any or all of prior embodiments in this paragraph up through the first embodiment in this paragraph wherein the modified UZM-14 has a $Si/Al_2$ ratio of 14 to 30. An embodiment of the invention is one, any or all of prior embodiments in this paragraph up through the first embodiment in this paragraph wherein the modified UZM-14 has a total pore volume in a range of 0.5 to 1.0 cc/g. An embodiment of the invention is one, any or all of prior embodiments in this paragraph up through the first embodiment in this paragraph wherein the modified UZM-14 has at least 5% of a total pore volume being mesopores having a diameter of 10 nm of less. An embodiment of the invention is one, any or all of prior embodiments in this paragraph up through the first embodiment in this paragraph wherein the modified UZM-14 has a cumulative pore volume of micropores and mesopores having a diameter of 100 Å or less of 0.25 cc/g or more. An embodiment of the invention is one, any or all of prior embodiments in this paragraph up through the first embodiment in this paragraph wherein the modified UZM-14 has a Collidine IR Bronsted acid site distribution greater than or equal to an area of 3/mg for a peak in a range of 1575 to 1700 $cm^{-1}$ after desorption at 150° C.

A second embodiment of the invention is a process for transalkylation of a feedstream comprising one or more of $C_7$, $C_9$, $C_{10}$ and $C_{11+}$ aromatics to obtain a product stream having an increased concentration of $C_8$ aromatics relative to that of the feedstream, comprising contacting the feedstream at transalkylation conditions with a catalyst comprising (a) a modified UZM-14 zeolite having a Modification Factor of 6 or more; (b) a binder selected from one or more of alumina, silica and silica-alumina; and, (c) a metal component comprising one or more elements selected from groups VIB(6), VIIB(7), VIII(8-10) and IVA(14) of the Periodic Table.

An embodiment of the invention is one, any or all of prior embodiments in this paragraph up through the second embodiment in this paragraph wherein the modified UZM-14 zeolite has one or more of a $Si/Al_2$ ratio of 14 to 30; a total pore volume in a range of 0.5 to 1.0 cc/g; at least 5% of a total pore volume are mesopores having a diameter of 10 nm of less; a cumulative pore volume of micropores and mesopores having a diameter of 100 Å or less of 0.25 cc/g or more; or a Collidine IR Bronsted acid site distribution greater than or equal to an area of 3/mg for a peak in a range of 1575 to 1700 cm$^{-1}$ after desorption at 150° C. An embodiment of the invention is one, any or all of prior embodiments in this paragraph up through the second embodiment in this paragraph wherein the feedstream further comprises benzene. An embodiment of the invention is one, any or all of prior embodiments in this paragraph up through the second embodiment in this paragraph wherein the feedstream further comprises $C_8$ aromatics. An embodiment of the invention is one, any or all of prior embodiments in this paragraph up through the second embodiment in this paragraph wherein the feedstream further comprises aromatic compounds having from 2 to 4 rings. An embodiment of the invention is one, any or all of prior embodiments in this paragraph up through the second embodiment in this paragraph wherein the feedstream further comprises a bottoms stream from the fractionation of $C_8$ aromatics from the transalkylation product stream. An embodiment of the invention is one, any or all of prior embodiments in this paragraph up through the second embodiment in this paragraph wherein the transalkylation conditions comprise one or more of a temperature from about 200° C. to about 540° C., a pressure from about 100 kPa to about 6 MPa absolute, or a space velocity from about 0.1 to about 20 hr$^{-1}$.

A third embodiment of the invention is a composition suitable for the conversion of aromatic hydrocarbons comprising a modified UZM-14 zeolite having a Modification Factor of 6 or more. An embodiment of the invention is one, any or all of prior embodiments in this paragraph up through the third embodiment in this paragraph wherein the modified UZM-14 zeolite has one or more of a Si/Al$_2$ ratio of 14 to 30; a total pore volume in a range of 0.5 to 1.0 cc/g; at least 5% of a total pore volume being mesopores having a diameter of 10 nm of less; a cumulative pore volume of micropores and mesopores having a diameter of 100 Å or less of 0.25 cc/g or more; or a Collidine IR Bronsted acid site distribution greater than or equal to an area of 3/mg for a peak in a range of 1575 to 1700 cm$^{-1}$ after desorption at 150° C. An embodiment of the invention is one, any or all of prior embodiments in this paragraph up through the third embodiment in this paragraph further comprising (a) an additional zeolitic component selected from one or more of MFI, MEL, EUO, FER, MFS, MTT, MTW, TON and FAU; (b) a binder selected from one or more of alumina, silica and silica-alumina; and, (c) a metal component comprising one or more elements selected from groups VIB(6), VIIB (7), VIII(8-10) and IVA(14) of the Periodic Table.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A catalyst suitable for conversion of aromatic hydrocarbons comprising a modified UZM-14 zeolite having a Modification Factor or 6 or more; wherein the modified UZM-14 modified is made by steps:
    contacting a calcined UZM-14 zeolite with one or more of: nitric acid, or oxalic acid to form an acid washed UZM-14 zeolite;
    contacting the acid washed UZM-14 with one or more of: a sodium hydroxide solution, or a sodium bicarbonate solution to form a caustic washed UZM-14 zeolite; and
    ion exchanging the caustic washed zeolite to form the modified UZM-14 zeolite.

2. The catalyst of claim 1 wherein the modified UZM-14 zeolite has a Si/Al$_2$ ratio of 14 to 30.

3. The catalyst of claim 1 wherein the modified UZM-14 zeolite has a total pore volume in a range of 0.5 to 1.0 cc/g.

4. The catalyst of claim 1 wherein the modified UZM-14 zeolite has at least 5% of a total pore volume being mesopores having a diameter of 10 nm of less.

5. The catalyst of claim 1 wherein the modified UZM-14 zeolite has a cumulative pore volume of micropores and mesopores having a diameter of 100 Å or less of 0.25 cc/g or more.

6. The catalyst of claim 1 wherein the modified UZM-14 zeolite has a Collidine IR Bronsted acid site distribution greater than or equal to an area of 3/mg for a peak in a range of 1575 to 1700 cm-1 after desorption at 150° C.

7. The catalyst of claim 1 wherein the catalyst further comprises an additional zeolitic component selected from one or more of MFI, MEL, EUO, FER, MFS, MTT, MTW, TON and FAU.

8. The catalyst of claim 1 wherein the catalyst further comprises a binder selected from one or more of alumina, silica and silica-alumina.

9. The catalyst of claim 1 wherein the catalyst further comprises a metal component comprising one or more elements selected from groups VIB(6), VIIB(7), VIII(8-10) and IVA(14) of the Periodic Table.

10. A catalyst suitable for the conversion of aromatic hydrocarbons comprising:
    a modified UZM-14 zeolite having a Modification Factor of 6 or more, wherein the modified UZM-14 zeolite comprises:
    a Si/Al$_2$ ratio of 14 to 30;
    a total pore volume in a range of 0.5 to 1.0 cc/g;
    at least 5% of a total pore volume being mesopores having a diameter of 10 nm of less;
    a cumulative pore volume of micropores and mesopores having a diameter of 100 Å or less of 0.25 cc/g or more; and
    a Collidine IR Bronsted acid site distribution greater than or equal to an area of 3/mg for a peak in a range of 1575 to 1700 cm-1 after desorption at 150° C.; wherein the modified UZM-14 modified is made by steps:
    contacting a calcined UZM-14 zeolite with one or more of: nitric acid, or oxalic acid to form an acid washed UZM-14 zeolite;
    contacting the acid washed UZM-14 with one or more of: a sodium hydroxide solution, or a sodium bicarbonate solution to form a caustic washed UZM-14 zeolite; and
    ion exchanging the caustic washed zeolite to form the modified UZM-14 zeolite.

11. The catalyst of claim 10 wherein the catalyst further comprises an additional zeolitic component selected from one or more of MFI, MEL, EUO, FER, MFS, MTT, MTW, TON and FAU.

12. The catalyst of claim 10 wherein the catalyst further comprises a binder selected from one or more of alumina, silica and silica-alumina.

13. The catalyst of claim 10 wherein the catalyst further comprises a metal component comprising one or more elements selected from groups VIB(6), VIIB(7), VIII(8-10) and IVA(14) of the Periodic Table.

\* \* \* \* \*